United States Patent
Asehnoune et al.

(10) Patent No.: US 9,709,501 B2
(45) Date of Patent: Jul. 18, 2017

(54) CYTOLOGICAL METHOD USING THE AUTO FLUORESCENCE OF WHITE CORPUSCLES FOR THE EARLY DIAGNOSIS AND THE MONITORING OF INFECTIONS

(75) Inventors: Karim Asehnoune, Nantes (FR); Marie-Pierre Fontaine-Aupart, Fresnes (FR); Sandrine Lecart, Gif s/yvette (FR); Antoine Monsel, Chatillon (FR); Antoine Roquilly, Nantes (FR)

(73) Assignees: UNIVERSITE DE NANTES (FR); UNIVERSITE PARIS-SUD 11 (FR); CENTRE NATIONAL DE LA RECHERCHE SCIENTIFIQUE (CNRS) (FR); Chu Nantes (FR)

( * ) Notice: Subject to any disclaimer, the term of this patent is extended or adjusted under 35 U.S.C. 154(b) by 64 days.

(21) Appl. No.: 14/006,455

(22) PCT Filed: Mar. 22, 2012

(86) PCT No.: PCT/EP2012/055127
§ 371 (c)(1),
(2), (4) Date: Mar. 26, 2014

(87) PCT Pub. No.: WO2012/127003
PCT Pub. Date: Sep. 27, 2012

(65) Prior Publication Data
US 2015/0037837 A1 Feb. 5, 2015

(30) Foreign Application Priority Data
Mar. 22, 2011 (FR) .................................. 11 52356

(51) Int. Cl.
G01N 21/64 (2006.01)
G01N 33/49 (2006.01)
G01N 15/14 (2006.01)
G01N 1/30 (2006.01)
G01N 33/50 (2006.01)
G01N 15/00 (2006.01)

(52) U.S. Cl.
CPC ........... *G01N 21/6486* (2013.01); *G01N 1/30* (2013.01); *G01N 15/1459* (2013.01); *G01N 33/49* (2013.01); *G01N 33/5091* (2013.01); *G01N 15/1463* (2013.01); *G01N 21/6458* (2013.01); *G01N 2015/008* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 6,289,236 B1 | 9/2001 | Koenig et al. | |
| 2007/0281036 A1* | 12/2007 | Landry | A61K 9/0019 424/497 |
| 2011/0008784 A1* | 1/2011 | Lee | C12Q 1/6881 435/6.11 |

FOREIGN PATENT DOCUMENTS

WO 99/50642 A1 10/1999

OTHER PUBLICATIONS

Liang et al., "Imaging Neutrophil Activation: Analysis of the Translocation and Utilization of NAD(P)H-Associated Autofluorescence During Anti body-Dependent Target Oxidation", Journal of Cellular Physiology 1992, vol. 152, pp. 145-156.*
Kindzelskii et al., "Fluorescence spectroscopic detection of mitochondrial flavoprotein redox oscillations and transient reduction of the NADPH oxidase-associated flavoprotein in leukocytes", European Biophysics Journal 2004, vol. 33, pp. 291-299.*
Kim Yeong Sic et al., "Neutrophils with Toxic Granulatin Show High Fluorescence with Bis(Zn2+-dipicolylamine) Complex," Annals of Clinical and Laboratory Science, vol. 39, No. 2, Apr. 2009, pp. 114-119, XP009150143, ISSN: 0091-7370.
B.M. Babior, "Oxidants From Phagocytes: Agents of Defense and Destruction," Blood 1984; 64: 959-966; From bloodjournal. hematologylibrary.org.
C. Brun-Buisson et al., "EPISEPSIS: a reappraisal of the epidemiology and outcome of severe sepsis in French intensive care units," Intensive Care Med. (2004) 30: 580-588.
Preliminary Search Report issued in corresponding French Application No. 1152356 issued on Jan. 25, 2012.
International Search Report issued in corresponding PCT/EP2012/055127 mailed on May 4, 2012.
Bu-Hong Li et al., "Autofluorescence excitation-emission matrices for diagnosis of colonic cancer," World J. Gastroenterol 2005; 11(25): 3931-3934; ISSN: 1007-9327.
Greg S. Martin et al., "The Epidemiology of Sepsis in the United States from 1979 through 2000," N Engl J Med 348: 1546-1554, Apr. 17, 2003, www.NEJM.org.

(Continued)

*Primary Examiner* — Renee Claytor
*Assistant Examiner* — Michelle F Paguio Frising
(74) *Attorney, Agent, or Firm* — Banner & Witcoff, Ltd.

(57) ABSTRACT

The present invention relates to an in vitro method for diagnosing the infectious state of an individual on the basis of a sample of white corpuscles arising from a biological specimen taken from an organ potentially infected by a pathogenic microorganism of said individual, comprising at least the following two steps: i) measuring the mean cellular intensity of the autofluorescence of said sample, and ii) comparing the intensity measured in step i) with a control value, so as to determine the infectious state of said individual. The diagnostic method of the invention uses a routine optical material making it possible to work in wavelength regions which are compatible with the cellular autofluorescence, and thus constitutes a rapid, reliable and inexpensive aid for the diagnosis or monitoring of an infection in an individual.

14 Claims, 3 Drawing Sheets

(56) References Cited

OTHER PUBLICATIONS

A. Mayevsky et al., "Mitochondrial function in vivo evaluated by NADH fluorescence: from animal models to human studies," Am J Physiol Cell Physiol 292: C615-C640, 2007.

Monica Monici, "Cell and tissue autofluorescence research and diagnostic applications," Biorechnology Annual Review, vol. 11, (2005), ISSN: 1387-2656.

Kenneth Murphy et al., "Innate Immunity 2," Janeway's Immunobiology. 7th Edition; pp. 1-72; http://www.garlandscience.com, (2008).

J. L. Pauly et al., "Fluorescent Human Lung Macrophages Analyzed by Spectral Confocal Laser Scanning Microscopy and Multispectral Cytometry," Microscopy Research and Technique 67: 79-89 (2005).

G. M. Palmer et al., "Autofluorescence Spectroscopy of Normal and Malignant Human Breast Cell Lines," Photochemistry and Photobiology, 2003, 78:(5): 462-469.

H. R. Petty et al., "Dissipative metabolic patterns respond during neutrophil transmembrane signaling," PNAS, Mar. 13, 2001, vol. 98, No. 6, 3145-3149.

\* cited by examiner

CYTOLOGICAL METHOD USING THE AUTO FLUORESCENCE OF WHITE CORPUSCLES FOR THE EARLY DIAGNOSIS AND THE MONITORING OF INFECTIONS

RELATED APPLICATION DATA

This application is a National Stage Application under 35 U.S.C. 371 of co-pending PCT application PCT/EP2012/055127 designating the United States and filed Mar. 22, 2012; which claims the benefit of FR application number 1152356 and filed Mar. 22, 2011 each of which are hereby incorporated by reference in their entireties.

PRIOR ART

Severe sepsis or serious bacterial infection remains a major cause of hospital morbidity-mortality, more specifically in intensive care units. Furthermore, its current incidence of 3 to 11 cases per 1,000 inhabitants in the United States has increased by 8.7% per year over the past ten years. 14.6% of admissions to French intensive care units are related to this pathology. In spite of many improvements in diagnostic and therapeutic procedures, hospital mortality related to severe sepsis is estimated at 35% in France. It is now clear that the time period separating the admission of the patient from the initiation of the antibiotic therapy constitutes a major prognostic factor of mortality. The goal is thus, in the $21^{st}$ century, to diagnose the infection as early as possible, which is a gauge of patient survival.

Moreover, one of the current issues in medicine is to be able to reduce the overall quantity of antibiotics used daily in order to fight the harmful effects of their widespread use (bacterial resistance and economic costs). The duration of antibiotic treatments for bacterial infections is currently at the heart of the principal debates. Rapid techniques for monitoring the infection in progress and thus of the effectiveness of the anti-infection treatments employed are thus necessary. These techniques will make it possible to stop treatments at the appropriate time and will give rise to a shortening of the duration of antibiotic treatments. In this way, they will lead to a reduction of the worldwide consumption of antibiotics.

However, the conventional microbiological techniques currently available, comprising direct examination and growth on nutritive media, do not provide a prompt response. Indeed, 24 to 48 hours are necessary to obtain a bacteriological diagnostic response. Similarly, gene amplification techniques (RT-PCR, for example) are very expensive because they rely upon sophisticated devices and they are not yet completely validated for diagnostic use.

To replace these microbiological or genetic techniques, there is thus an urgent need develop reliable and inexpensive methods making it possible to diagnose infections rather early in their development, and much faster than is currently possible.

However, it is known that the host's response to microorganisms is established in the first minutes of the infection: it is in fact nearly immediate. White blood cells, key cells of innate immunity, play a fundamental and very early role in the recognition and destruction of pathogenic agents. These defense mechanisms of the host against microbes (bacteria and viruses) are dependent upon specific receptors called Toll-like receptors (TLRs). Several of these TLRs play a central role in the recognition of bacteria: TLR4, for example, recognizes Gram-negative bacteria membrane components such as lipopolysaccharide (LPS), whereas TLR2 recognizes Gram-positive bacteria elements such as peptidoglycan (PGN). TLR3, 7 and 8 are endosomal receptors that recognize viral RNA. Once stimulated, these TLRs have the common characteristic of leading to the activation of the nuclear transcription factor NF-κB and the production of NF-κB dependent proinflammatory cytokines, such as tumor necrosis factor alpha (TNF-α) and interleukin-6 (IL-6). Furthermore, another signaling pathway constitutes an important mechanism of defense of innate immunity: the N-formyl-L-methionyl-L-leucyl-L-phenylalanine (fMLP) receptor pathway. This peptide, a product of the breakdown of bacterial proteins, activates a G protein coupled receptor leading to a cascade of activation of intracytoplasmic kinases resulting in the phosphorylation of subunits whose assembly forms NADH-oxidase. This membrane enzyme complex enables monocytes and polymorphonuclear neutrophils (PNN) to produce reactive oxygen species (ROS) by oxidizing NADH to NAD. These ROS participate in the bactericidal activity of phagocytes.

The present Inventors show herein that it is possible to use, in quite particular experimental conditions, the autofluorescence of these white blood cells to reveal the early immunological activity which is established during the microbial infection (and thus the infectious state of an individual). The diagnostic method of the invention uses a routine optical material making it possible to work in wavelength ranges compatible with cellular autofluorescence, and thus constitutes a rapid, reliable and inexpensive aid to the diagnosis of an infection in an individual. It also makes it possible to very rapidly measure the effectiveness of anti-infection therapies established beforehand.

SUMMARY OF THE INVENTION

The present invention first relates to an in vitro method for diagnosing the infectious state of an individual based on a sample of white blood cells arising from a biological specimen from said individual, comprising at least the following steps:
  i) measuring the mean cellular autofluorescence intensity of said sample, and
  ii) comparing the intensity measured in step i) with a control value, so as to determine the infectious state of said individual.

In a particular embodiment, the white blood cells of said sample are selected from monocytes and/or polymorphonuclear neutrophils. In this embodiment of the invention, when the state of said individual is infectious, said individual is suffering from a bacterial, viral or fungal infection, preferably bacterial.

Preferably, said biological specimen is a fluid arising from a potentially infected organ of said individual; more preferably this sample is a pulmonary fluid, ascites fluid, cerebrospinal fluid, blood sample or any other biological fluid arising from a potentially infected organ.

In a preferred embodiment, the autofluorescence intensity of the cells of said sample is measured on chemically fixed cells, by means of a fluorescence microscope, a flow cytometer, a spectrofluorometer or any other optical device capable of measuring fluorescence.

In a most preferred embodiment, the sample of cells is prepared in a monolayer on slide of transparent material, preferably glass, prior to step i), according to a method comprising at least the following steps:
  a) depositing cells of said sample in at least one cytocentrifugation system, b) centrifuging the device obtained in step a), preferably at about 600 rpm for about 5 minutes, so as to project the cells on said slide,
c) fixing the cells thus projected on the slide to form a cell spot, with at least one drop of about 4% paraformaldehyde (PFA), preferably for about 10 minutes,
d) rinsing the previously fixed cell spot, preferably with PBS buffer,
e) allowing the previously rinsed cell spot to dry,
f) adding to the previously dried cell spot at least one drop of a mounting medium compatible with the observation of fluorescence,
g) affixing a transparent cover slip, preferably made of glass, on the cell spot arising from step f).

When the white blood cells of said sample are mostly monocytes, the state of said individual is infectious if the autofluorescence intensity measured in step i) is significantly greater than the control value.

When the white blood cells of said sample are mostly polymorphonuclear neutrophils, the state of said individual is infectious if the autofluorescence intensity measured in step i) is significantly lower than the control value.

DETAILED DESCRIPTION OF THE INVENTION

Figure 1:
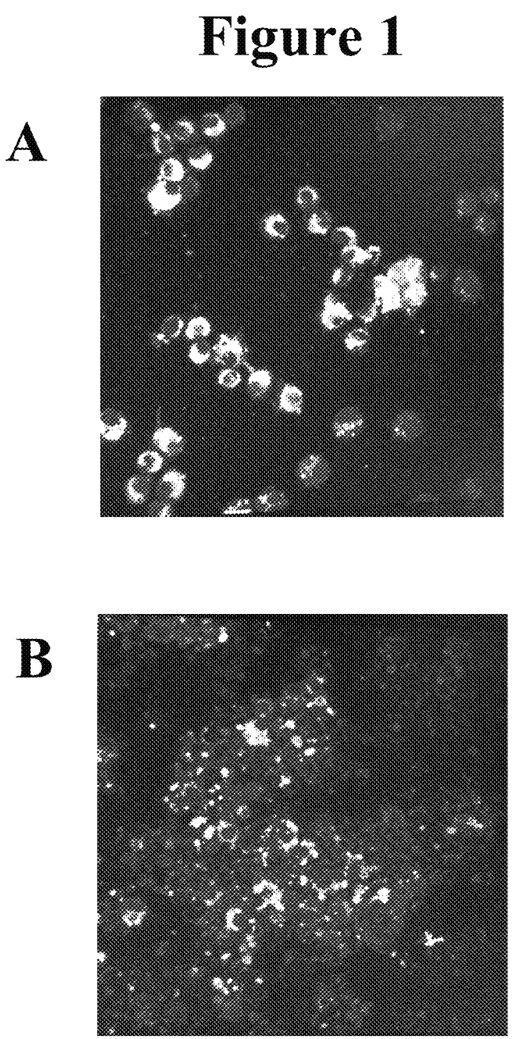
FIG. 1 consists of two images (A, B) taken by a confocal microscope, revealing the autofluorescence of monocytes and polymorphonuclear neutrophils arising from cytological slides of bronchoalveolar lavage (BAL) in a murine model of *Staphylococcus aureus* pneumonia.
Figure 2:
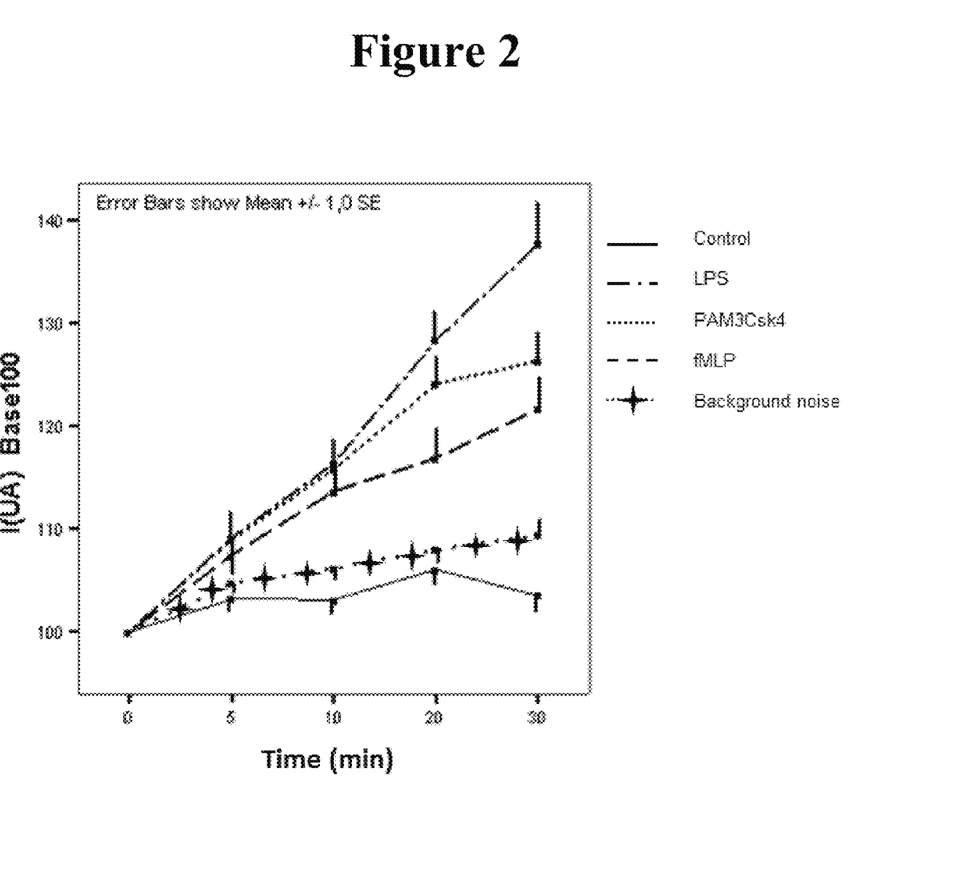
FIG. 2 represents the variations of the autofluorescence intensity ($I_f$) as a function of time of human monocytes according to various stimulation conditions.
Figure 3:
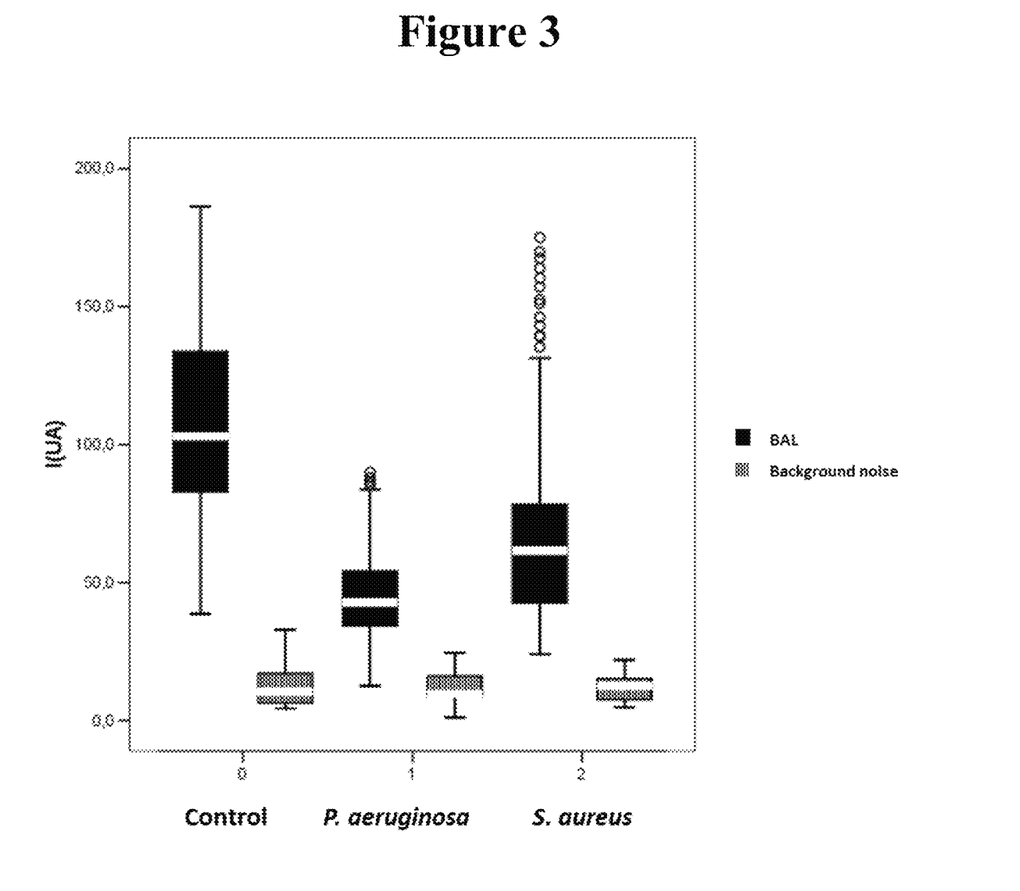
FIG. 3 illustrates the autofluorescence intensity ($I_f$) of monocytes-macrophages and PNN sampled in bronchoalveolar lavages (BAL, in black) in murine models of *Pseudomonas aeruginosa* or *Staphylococcus aureus* pneumonia. Background noise is represented by bars.

The method of the present invention uses the autofluorescence of special cells of the immune system in order to diagnose the presence of bacterial and/or viral agents in an individual at risk. Infectious bacterial and/or viral pathogens are capable, via the activation of TLRs, of causing early metabolic activity in these immune cells. This metabolic activity may be correlated with variations in the concentration of NAD(P)H, one of the essential coenzymes involved in cellular energy metabolism, characterized by its intracellular autofluorescence (Mayevsky A et al., *Am J. Physiol. Cell Physiol.* 2007).

This endogenous fluorescent signal, usually a nuisance in the context of studies using fluorescent probes, is already exploited in the field of cancer research and cellular metabolism, its study making it possible to distinguish various metabolic states (U.S. Pat. No. 6,289,236, Palmer G M et al., *Photochem Photobiol* 2003; Li B H et al., *World J. Gastroenterol.* 2006). However, no diagnostic testing using the autofluorescence of cells of the immune system, and in particular those identified by the present Inventors, has ever been described or suggested.

In this field, only two studies have been carried out: first, the team of Petty et al. has shown the temporal and spatial oscillation of the autofluorescence signal in polymorphonuclear neutrophils stimulated by immune agonists, by attempting to characterize the various states of activation of these cells (Petty H. R. et al., PNAS 2001; 98:3145-3149). This study recalls that the autofluorescence of neutrophils and monocytes is mainly due to the presence of NADH which undergoes temporal oscillations and significant intracellular displacements, which can be induced by bacterial activation signals. It is important to note that the signal studied is a signal of undulatory variation of the autofluorescence intensity in time and space on a temporal scale of 0.1 µs to 20 µs, and on a spatial scale of a few microns. The space-time undulatory changes thus take place in an infinitesimal temporal interval succeeding the in vitro immune stimulation of PNN (several µs after stimulation by the immune agonist concerned). These results thus discourage the use of these autofluorescence fluctuations, too short in time and too localized in space, for a diagnostic method. Indeed, from the perspective of a diagnostic method, it is necessary for the metabolic state modified since time T1 of infection is stable over time and quantifiable at time T2 when the sample is taken. As the time interval separating the stimulation of the cells of interest and the demonstration of the activated metabolic state represents in practice a few hours to several days, it is thus absolutely incompatible with the time scales described by Petty et al.

The second study relates to the demonstration of the effect of tobacco on the autofluorescence of macrophages of the lung. Pauly et al. have indeed identified that smoking increases the intensity of this autofluorescence (Pauly J. L. et al., *Microsc Res Tech* 2005).

Furthermore, the international patent application WO 99/50642 describes a method for diagnosing infections, based on the exploitation of the autofluorescence of whole plasma of patients suffering from a viral infection (AIDS virus or hepatitis virus) to establish spectral emission characteristics distinguishing the plasma of sick patients from that of controls. The method of the present invention does not exploit the autofluorescence of plasma (as proposed by WO99/50642), but the autofluorescence of specific cells, namely immune cells (and, preferably, among these cells, monocytes and polymorphonuclear neutrophils) arising from whole blood or potentially infected organs.

The present Inventors have developed for the first time an experimental protocol making it possible to exploit the autofluorescence of white blood cells, and in particular the modulations of this autofluorescence related to their activation. They thus propose a reproducible, reliable and effective system for evaluating the infectious state of target individuals.

In a first aspect, the present invention thus relates to an in vitro method for diagnosing the infectious state of an individual based on a sample of immune cells arising from a biological specimen from said individual, said method comprising at least the following steps:
i) measuring the mean cellular autofluorescence intensity of said sample, and
ii) comparing the intensity measured in step i) with a control value, so as to determine the infectious state of said individual.

In the context of the present invention, when the state of an individual is "infectious," said individual is infected with a microorganism, preferably a bacterium, virus or fungus (yeast or filamentous). In a more preferred manner, said individual suffers from a bacterial infection. This state can already have been diagnosed before and the individual can be subjected to an anti-infection treatment (antibiotic). In this case, the diagnostic method of the invention is intended to evaluate if the infection is still present and/or if the treatment can be stopped.

Herein, "individual" refers to an animal or a mammal, and in particular man.

A "biological" specimen is defined in the present invention as any specimen of biological fluid, preferably arising from potentially infected organs and thus containing white blood cells. It is possible in the context of the present invention to take for example a sample of pulmonary fluid (in the case of pneumonia), of ascites (in infections of ascites fluid), of cerebrospinal fluid (in meningitis) or of blood, or of any other potentially infected organ.

In the context of the present invention, "obtaining a sample of cells arising from a biological specimen" consists of 1) taking a sample of biological fluid from an individual, preferably from an organ of an individual, and 2) specifically in the context of a blood sample, purifying from this sample the cells of interest by conventional cell biology methods, in order to obtain the sample of purified cells.

It should be noted that the optional step of cellular purification to preferentially obtain cells of interest is not necessary when a biological fluid other than blood is used. Indeed, for the other sampled fluids (pulmonary, cerebrospinal or ascites fluid), in the case of infection, these fluids will contain in large majority cells of interest (PNN and monocytes), and thus there is no need to purify them.

In the case of a blood sample, the volume taken is preferably at least 10 ml to 20 ml, so as to obtain sufficient cells of interest after purification. In the case of a sample of a fluid from an organ, a few ml are enough (500 µl to 1 ml per cytospin well).

The sample of cells that can be used in the diagnostic method of the invention can be either preserved at room temperature to be used extemporaneously (in practice, less than 5 hours after the sample is taken) or preserved at a temperature of 4° C. in order to preserve the integrity of the cells until the operations of cell purification/isolation, fixing and/or measurement of autofluorescence intensity.

In the context of the presents invention, the "mean cellular autofluorescence intensity" measured in step i) of the diagnostic method of the invention is the total autofluorescence intensity for a cell suspension or a median cell value obtained on at least about 50 cells, preferably about 100 cells. It is then advisable to 1) subtract from this total value the value of autofluorescence due to possible contaminating cells, and 2) divide this remaining intensity by the number of cells of interest (monocytes or polymorphonuclear neutrophils) present in the sample studied. This final value will be the mean cell intensity in the context of the present invention.

Numerous software packages make it possible today to instantaneously obtain a quantification of cellular autofluorescence levels and to calculate the mean for a large number of cells (for example, MetaMorph, ImageJ, Imaris or any other image processing software known to persons skilled in the art).

The "control" value (or "standard") to which it is advised to compare the autofluorescence intensity of the individual to be tested is the mean cellular autofluorescence intensity obtained from a large number of isolated cells arising from several healthy individuals not having had treatment for at least 7 days (notably neither antibiotic nor anti-inflammatory treatment), not exhibiting any declared detectable infection (no signs or symptoms of infection, such as, for example: fever, aches, pains, etc.). This control value is typically calculated on at least 100 cells isolated from at least 5 healthy individuals. It is calculated beforehand using the standard experimental parameters that will be used for the patient tested (notably in terms of optical material used, cell fixation method, excitation and emission wavelengths, temperature, pH, etc.).

Immune cells, also called "white blood cells" or "leukocytes," are human blood cells containing a mono or multilobed nucleus, which play essentially a role in the defense of the organism against foreign agents in the context of innate immunity. Among white blood cells, mononuclear cells (B-cells, T-cells, monocytes, macrophages) are distinguished from polymorphonuclear cells (or "granulocytes," which include neutrophils, eosinophils and basophils) (Keneth M. Murphy, Paul Tavers, & Mark Walport, *Janeway's Immunobiology.* $7^{th}$ Edition)

In a preferred manner, in the context of the present invention, the white blood cells of said sample are selected from monocytes and/or polymorphonuclear neutrophils.

In a variant of the diagnostic method of the invention, the cell sample contains preferably at least about 80%, preferably about 90% of PNN, still more preferably at least about 95% of PNN.

Certain biological fluids taken directly from organs are known to contain only PNN. For example, fluids from bronchoalveolar lavage as well as from ascites contain mostly PNN (E. Pilly, *Maladies infectieuses et tropicales*, $22^{nd}$ edition, 2010). In this case a preliminary purification step will not be necessary.

Preferably, the sample of biological fluid used in the present invention does not undergo a purification step because it naturally contains at least about 80%, preferably about 90% of PNN, still more preferably at least about 95% of PNN. The sample of biological fluid is thus preferentially a sample of BAL, ascites or cerebrospinal fluid (CSF).

Nevertheless, if a purification step were required to obtain a cell sample that can be used in the method of the invention (notably in the case of a blood sample), it is preferable first to isolate the polynucleated blood cells and then, by techniques known to persons skilled in the art, such as, for example, selection by separation on a magnetic column (anti-CD16), to obtain the polymorphonuclear neutrophils. To obtain a sample of polynucleated cells from a biological fluid, it is advisable to use one of the techniques well-known to persons skilled in the art. For example, mention may be made of the density gradient technique and then withdrawal of the lower band, which corresponds essentially to polymorphonuclear cells (see the Cederlane®, Tebu-bio technique described in the examples below).

Most cases of pneumonia have mostly neutrophilic formulas (mostly PNN). However, some are mostly monocytic or mixed (50/50). These proportions depend on the pathogenic agent responsible for the pneumonia, on the individual and/or on the more or less advanced stage of pneumonia. All the biological fluids referred to in the invention (blood, pulmonary fluid, cerebrospinal fluid, ascites fluid) can contain mostly monocytes in certain particular cases of infection.

In another variant of the diagnostic method of the invention, the cell sample thus contains preferably at least about 80%, preferably about 90% of monocytes, still more preferably at least about 95% of monocytes.

Preferably, the sample of biological fluid used in the present invention does not undergo a purification step because it naturally contains at least about 80%, preferably about 90% of monocytes, still more preferably at least about 95% of monocytes (in the case of pulmonary fluid, cerebrospinal fluid or ascites fluid).

If a purification step were required (the sample is of blood, for example), monocytes can be isolated from mononucleated cells by techniques well-known to persons skilled in the art. For example, positive selection by separation on a magnetic column (anti-CD14 antibody) can be carried out. To obtain a sample of mononucleated cells (lymphocytes, monocytes, macrophages) from a biological fluid, it is preferable to use cell biology techniques well-known to persons skilled in the art. For example, the density gradient technique can be used, and then the upper band comprising these cells can be withdrawn (see the Cederlane®, Tebu-bio technique described in the examples below).

Fluorescence is the property in which a molecule emits a photon in order to return from its excited state (following the absorption of another photon) to its ground state. Cells contain molecules that can become fluorescent when they are excited with rays of wavelengths in the visible or ultraviolet (UV) range. This emission of fluorescence, emanating from endogenous fluorophores, is an intrinsic property of cells called "autofluorescence" or "endogenous fluorescence" and must be distinguished from the fluorescence signals obtained by the addition of exogenous markers. The known fluorophores are: aromatic amino acids, lipophilic dyes, NADPH, flavins and porphyrins. Autofluorescence does not require specific marking (Monici M., *Biotechnol Annu Rev.* 2005).

The light source used in the method can thus take any form of optical tool as long as it is capable of providing a sufficiently powerful intensity of light in the wavelength range concerned. Although LASER UV (argon) sources are capable of providing an incidental beam with such characteristics, other optical tools capable of providing wavelength ranges compatible with the excitation of cellular NADH can also be used. This is the case with certain lamps (mercury, halogen, etc.) of LASER diode and white LASER lamps (delivering a continuous emission spectrum over a broad range of wavelengths).

To reveal and measure biological autofluorescence, it is possible to use 1) cells in suspension, i.e., cells that are not attached to a support and that move freely in a suitable liquid medium, or 2) cells fixed on a transparent support, preferably a glass slide.

According to a particular embodiment of the invention, the autofluorescence intensity of the cells of said sample is measured on cells in suspension. In this particular embodiment, the autofluorescence can be measured with systems that measure fluorescence without an observer being able to see these cells, for example by flow cytometry, spectrophotometry or microspectrofluorimetry.

In this case, the mean autofluorescence intensity is measured automatically by systems (flow cytometers, spectrophotometers) that measure the total fluorescence of each sample.

In another particular embodiment of the invention, the autofluorescence intensity of the cells of said sample is measured on chemically fixed cells placed on a slide compatible with the observation of fluorescence, preferably a transparent glass slide, and the autofluorescence is then measured with conventional fluorescence microscopy (epifluorescence microscopy), confocal microscopy or two-photon microscopy apparatuses.

The mean autofluorescence intensity is then measured by means of image processing software, the image being obtained from a suitable device such as a camera coupled to a microscope.

Without wanting to be limited by it, in the context of the present invention, a flow cytometer, a conventional spectrophotometer, or any type of microscope making it possible to obtain a fluorescence signal using intensity imaging or photon counting can be used.

In a preferred embodiment of the invention, the autofluorescence intensity is measured for cells fixed on a transparent glass slide, using a conventional epifluorescence microscope.

In a still more preferred embodiment of the invention, the autofluorescence intensity of the cells of said sample is measured using an epifluorescence microscope that excites the cells with a wavelength ranging from about 300 nm to about 600 nm, preferably ranging from about 350 nm to about 450 nm. This excitation is carried out preferably by using a laser UV source.

Furthermore, the autofluorescence intensity of the cells of said sample measured in step i) of the present invention is preferably that emitted at a wavelength ranging from about 400 nm to about 700 nm, preferably ranging from about 450 nm to about 600 nm.

In a very particular embodiment, the autofluorescence intensity of the cells of said sample is measured in step i) of the diagnostic method of the invention using a confocal fluorescence microscope with a continuous argon UV laser source, a photomultiplier sensitive in the wavelength range of about 400 nm to about 550 nm, an open pinhole and a X63/1.4 oil immersion objective.

In one embodiment of the invention, the mean cellular autofluorescence intensity is measured on living cells.

In a preferential manner, these living cells were isolated from an organ, and were resuspended preferably in a liquid medium in a culture device that can be transferred to an optical exploitation tool (such as the cell culture well or LabTek® used in the first experimental phase described below).

In this case, the present Inventors have shown that it was important, to measure autofluorescence on living cells in a reliable and reproducible manner, to maintain the pH and the temperature of the culture medium at a constant value (pH preferably between 7 and 8, still more preferably 7.4, and temperature maintained at 37° C.) throughout the measurement of autofluorescence. Otherwise, the autofluorescence intensity values measured will be less reliable and less reproducible.

However, in a preferred embodiment of the invention, the cellular autofluorescence intensity of the sample is measured on cells chemically fixed, i.e., fixed in a particular cellular metabolic state, for example using paraformaldehyde.

In this embodiment, the cells of the biological specimen are chemically fixed as quickly as possible, preferably less than 5 hours, after the biological sample is taken. Indeed, by fixing the white blood cells in a certain state, it is instantaneous cellular metabolic state that is studied. This makes it possible to avoid all the technical difficulties related to the perpetuation of a living cellular state which a method studying living cells would require. This is why it is important to minimize time between the fixing of the cells of the sample and the taking of the sample. The particular case of blood samples, in which the purification step can take place only on living cells and thus before any fixing step, is noted.

The present Inventors tested several fixing methods and several slide mounting systems in order to obtain a reliable measurement of autofluorescence for the two types of immune cells below (monocytes and PNN, see example 3 below). In this way, they identified a common cell sample treatment protocol suited to the constraints of the method of the invention, i.e., one that ensures a sufficient autofluorescence signal making it possible to obtain reliable and reproducible results for these two cell types.

In this preferred embodiment, the cells must be prepared in a monolayer by cytocentrifugation on a glass microscope slide before being fixed on said slide with paraformaldehyde (PFA), washed, dried, and then finally mounted in a mounting medium compatible with the observation of fluorescence before being covered with a glass cover slip.

More precisely, in this particular embodiment of the method of the invention, the sample of cells is prepared in a monolayer on a slide of transparent material, preferably made of glass, prior to step i), according to a method comprising at least the following steps:
- a) depositing cells from said sample in at least one cytocentrifugation system,
- b) centrifuging the device obtained in step a), preferably at about 600 rpm for about 5 minutes, so as to project the cells on said slide,
- c) chemically fixing the cells thus projected on the slide to form a cell spot, with at least one drop of about 4% paraformaldehyde (PFA), preferably for about 10 minutes,
- d) rinsing the previously fixed cell spot, preferably with PBS buffer,
- e) allowing the previously rinsed cell spot to dry,
- f) adding to the previously dried cell spot at least one drop of a mounting medium compatible with the observation of fluorescence,
- g) affixing a transparent cover slip, preferably made of glass, on the cell spot arising from step f).

In this quite particular embodiment, step i) of measuring the mean cellular autofluorescence intensity of the sample is performed using a fluorescence microscope.

During step a), the number of cells introduced into the well of the centrifugation system is advantageously between 500,000 and 1,000,000 in 500 µl to 1 ml of volume per well.

These cells are deposited in a cytospin-type cytocentrifugation system (for example, that marketed by Thermo Electron Corporation under the name Shandon Cytospin®) consisting of a well coupled to a transparent microscope slide, preferably made of glass.

Cytocentrifugation is today a well-known technology that makes it possible to deposit cells of interest placed in the well in a well-defined area on a microscope slide of transparent material, preferably made of glass, in a monolayer, and allows the absorption of residual liquid by the sample chamber filter. During the operation of the centrifuge, the rotatory movement of the instrument tilts the wells in a straight position and centrifuges the cells onto the deposition area of the slide, providing all the cells with the same possibility of being exposed.

The transparent slide (or "microscope slide") on which the cells of interest are deposited is preferably a glass slide suited to the analysis of cellular fluorescence, of thickness ranging between 1.2 mm and 1.5 mm, preferably 1.5 mm, such as those marketed by Fisher Scientific.

The device obtained in step a) is then centrifuged. This centrifugation of step b) is carried out between 400 and 1000 rpm, preferably at about 600 rpm (41 g) for about 5 minutes.

To carry out step c), the microscope slide is then taken out of the centrifuge, and the cell spot obtained after step b) is chemically fixed with paraformaldehyde (PFA) solution, diluted in PBS solution at a concentration ranging between about 2% and 6%, preferably about 4%.

The quantity of PFA is advantageously about 15 µl of paraformaldehyde (PFA) for about $10^6$ cells, or a 1 ml drop of PFA on the cell spot projected on the slide.

The PFA fixing time is between 2 minutes and 20 minutes, and is preferably about 10 minutes.

The fixed cell spot is then rinsed, for example with PBS, to eliminate the remaining PFA (step d)). Three washes are generally required in order to effectively eliminate the remaining PFA.

During step e), the cell spot is dried completely, for example with air, for the required time, about 10 minutes at room temperature.

The cell spot is then covered with a drop (preferably 20 µl) of a mounting medium compatible with the observation of fluorescence. This medium is, for example, the "Pro-Long® Gold" or "Fluoromount" mounting medium, or "Vectashield Slow Fade." Preferably, this medium is "Pro-Long® Gold."

Lastly, the sample must then be covered with a cover slip suitable to the measurement of fluorescence, preferably made of glass, typically from 0.13 to 0.17 mm in thickness, such as those offered by Fisher Scientific.

The present Inventors have shown that, by comparing the mean cellular autofluorescence intensity of the tested patient's sample with the so-called "control" value, when the white blood cells of said sample are mostly monocytes, the state of said individual is infectious if the autofluorescence intensity measured in step i) is significantly greater than the control value.

In other words, if a sample of cells comprising at least about 70%, preferably at least about 80%, still more preferably at least about 90% of monocytes emits an autofluorescence signal significantly greater than the control value, then the individual from whom the sample of biological fluid was taken is suffering from (or is still infected by) a bacterial, viral or fungal infection.

The term "significantly greater" means, in the context of the present invention, that the ratio [mean cellular intensity of the patient]/[control value] is at least about 1.2, advantageously between about 1.3 and 3, in a preferred manner between about 1.5 and 2.

The present Inventors have shown that, conversely, by comparing the mean cellular autofluorescence intensity of the sample from the patient tested with the so-called "control" value, when the white blood cells of said sample are mainly polymorphonuclear neutrophils, the state of said individual is infectious if the autofluorescence intensity measured in step i) is significantly lower than the control value.

The difference in result between the two cell populations can be explained by, among other things, the very different metabolic nature of these two cells.

In other words, if a sample of cells comprises at least about 70%, preferably at least about 80%, still more preferably at least about 90% of polymorphonuclear neutrophils, and emits a autofluorescence signal that is significantly lower than the control value, then the individual from whom the sample of biological fluid was taken is suffering from (or is still infected by) a bacterial, viral or fungal infection.

The term "significantly lower" means, in the context of the present invention, that the ratio [mean cellular intensity of the patient]/[control value] is at most about 0.8, advantageously between about 0.1 and 0.7, in a preferred manner between about 0.1 and 0.6.

In a second aspect, the present invention thus relates to a method for preparing a fixed cell sample intended to be used in the diagnostic method as described above, and comprising the following steps:
- a) depositing the cells in at least one cytocentrifugation system, b) centrifuging the device obtained in step a), preferably at about 600 rpm (41 g) for about minutes, so as to project cells on said slide, c) chemically fix the cells thus projected on the slide, forming a cell spot, with at least one drop of about 4% paraformaldehyde (PFA), preferably for about 10 minutes, d) rinsing the previously fixed cell spot, preferably with PBS buffer, e) allowing the previously rinsed cell spot to dry, f) adding to the previously dried cell spot at least one drop of a mounting medium compatible with the observation of fluorescence, and g) affixing a transparent cover slip, preferably made of glass, on the cell spot arising from step f).

Steps a) to g) as are described above.

Advantageously, this method of preparation can be carried out automatically by means of robots capable of carrying out these steps sequentially.

Another advantage of the diagnostic method of the invention rests in the fact that it can be carried out entirely automatically with a single compact apparatus:

1) automatic preparation of the sample from the patient
2) automatic measurement of mean cellular autofluorescence of the samples,
3) comparison of the values to the control values,
4) generation of the result: presence of a bacterial, viral or fungal agent in said patient.

This automated system has the advantage of being much faster than the microbiological techniques currently used and much less expensive than the genetic techniques aimed at identifying the presence of an infectious agent, which, moreover, remain not completely validated notably in the case of bacterial infection.

EXAMPLES

1) Reagents and Materials Used

Whole blood was taken in 4.5 ml BD Vacutainer® tubes with 0.5 ml of 3.8% (w/v) sodium citrate. The culture medium, RPMI 1640, comes from Invitrogen® (Paisley, United Kingdom).

Density gradient: Lympholyte-Poly® comes from Cedarlane Tebu-Bio® (Le Perrey-en-Yvelines, France). The MACS® kit for insolating monocytes and anti-CD14 antibodies come from Miltenyi Biotec® (Paris). Purified lipopolysaccharide (LPS) of *Escherichia coli* 0111: B4 comes from Sigma® (Saint Louis, Mo., United States of America). Pam3Csk4 (hereafter PAM) comes from InvivoGen® (San Diego, United States of America). fMLP comes from Sigma-Aldrich® (St Quentin Fallavier, France). Sterile observation chambers for Lab-Tek® confocal microscopy come from Brands Products® (United States of America). Sterile 24-well plates and conical tubes come from Falcon®, Becton Dickinson Labware (Europe, Le Pont de Claix, France). The specific mounting medium ProLong® Gold Antifade reagent comes from Invitrogen (ref.: P36934). The centrifuge used for cytocentrifugation and to project the cell samples on a slide is a Shandon Cytospin® centrifuge.

The microscope available at the imaging unit of the biomedical photonics center of Orsay is a Leica® TCS SP5® confocal microscope. It has of 4 continuous lasers (2 helium-neon lasers, 633 nm and 543 nm, a visible argon laser, 458 nm, 476 nm, 488 nm and 514 nm, and an argon UV laser, 351 nm and 364 nm) and a high pulse rate titanium/sapphire infrared laser. The first acquisition mode used is that of the analysis of fluorescence intensity ($I_f$) quantified in AU.

2) Conditions of NAD(P)H Autofluorescence Signal Acquisition

Based on the initial cellular observations, the optimal optical experimental conditions giving the best compromise in terms of image resolution of NAD(P)H autofluorescence intensity and of deterioration of the biological sample were set.

For the acquisition of the fluorescence intensity signal, the continuous argon UV laser source was used ($\lambda$=364 nm, P=1.3 mW), as well as a photomultiplier (gain=1250 V) in the wavelength range of 400 nm to 550 nm, with a pinhole opened to the ⅓ of the maximum opening, with a X63 oil immersion objective. A mean of 4 images with a resolution of 1024 pixels/1024 pixels for a final size of 246 µm/246 µm was applied to display the image in $I_f$.

3) Demonstration of the Exploitability of the Cytological Autofluorescence Obtained from Human Monocytes and PNN Stimulated Ex Vivo.

After the informed consent of the volunteers, 20 ml of whole blood was taken from 8 healthy volunteers. The population of healthy volunteers was comprised of males and females, from 25 to 60 years of age, having not taken any treatment for at least 7 days, notably not antibiotics nor anti-inflammatories. They did not exhibit infections apparently in the course of evolution. Their blood was obtained by puncture of the vein on the inside of the elbow.

For Obtaining Monocytes:

From each blood sample (20 ml), mononucleated cells (MNC) were isolated using a density gradient technique well-known to persons skilled in the art (Lympholyte-Poly®, Cedarlane Tebu-Bio®, Le Perrey-en-Yvelines, France). This technique makes it possible to obtain two distinct bands of cells, an upper band of MNC (lymphocytes and monocytes) which was withdrawn and a lower band of polynucleated cells, comprised essentially of polymorphonuclear neutrophils. The monocytes were then isolated from the MNC using a positive selection technique with separation on a magnetic column (MACS®, Miltenyi Biotec, Paris). The blood monocytes were then suspended in RPMI 1640+4% human serum+penicillin G (100 U/ml) and streptomycin (100 ng/ml) (Valbiotech).

For Obtaining PNN:

From each blood sample (12 ml), centrifugation on Ficol (40 minutes at 1600 rpm at +4° C.) made it possible to recover the lower band suspended in RPMI+human serum (4%)+EDTA (5%). Two washes were then carried out in this medium (10 minutes at 1600 rpm at +4° C.). Then a depletion of eosinophils by the addition of an anti-CD16 antibody was carried out according to a negative selection by separation on a magnetic column (MACS®, Miltenyi Biotec, Paris). The PNN were then suspended in RPMI 1640+4% human serum+penicillin G (100 U/ml) and streptomycin (100 µg/ml) (Valbiotech).

The two cell populations thus obtained (PNN and monocytes) were incubated for 90 minutes in the presence of immune agonists with a cell density of $10^6$ cells/ml. LPS was used at a final concentration of 50 µg/mL, PAM at a final concentration of 10 µg/mL, and fMLP at a final concentration of $10^{-6}$ mol/l.

After 90 minutes, a volume of 500 µl of the cell sample ($5 \cdot 10^5$ cells) was delicately withdrawn and deposited in a well coupled to a cytology slide in accordance with the Cytospin® device. A centrifugation-slide projection cycle was carried out at 600 rpm for 8 minutes with low acceleration-deceleration. The cell spot projected on the slide was fixed with a drop of 4% paraformaldehyde (PFA) for 10 minutes followed by 3 delicate rinses with standard PBS buffer solution. After complete drying, a 20 µl drop of ProLong® Gold Antifade reagent mounting medium freshly unfrozen was deposited on the fixed cell spot. A glass cover slip was then delicately placed on the drop of mounting medium while taking care to avoid any formation of air bubbles.

The cytology slides thus obtained were then observed using a confocal laser scanning microscope. For the acquisition of the fluorescence intensity signal, the continuous argon UV laser source was used ($\lambda=364$ nm, P=1.3 mW), as well as a photomultiplier (gain=1250 V) in the wavelength range of 400 nm to 550 nm, with a pinhole opened to the ⅓ of the maximum opening, and a X63 oil immersion objective. A mean of 4 images at a resolution of 1024 pixels/1024 pixels for a final size of 246 µm/246 µm was applied to display the image in $I_f$.

A significant increase in the $I_f$ of 10% to 18% is noted for the stimulated monocytes in relation to the control monocytes. A significant decrease in the $I_f$ (by a factor of 2) is further noted for the stimulated PNN in relation to the control PNN. There thus seems to be for the stimulated monocytes, as for the stimulated PNN, a difference in the autofluorescence $I_f$ in relation to the control monocytes or PNN. This "PNN-monocyte" contrast in the direction of the variation of $I_f$ of the stimulated cells is probably explained by fundamental differences in cellular energy metabolism and the means of defense against the pathogen.

With regard to the cytocentrifugation protocol (cytospin), several rotation speeds were tested (300 rpm, 600 rpm, 800 rpm) as well as several centrifugation times (6 min, 8 min, 10 min). The combination of a force of 600 rpm for 8 minutes proved to perform best and to be the most advantageous in terms of cytological sample preparation time.

Several protocols for fixing the cell samples were tested, notably 4% PFA and alcohol spray containing ethanol (Merckofix Spray, Merck art), as well as fixation at −20° C. in acetone or ethanol or methanol. The best results in terms of the exploitability of the cellular autofluorescence were noted with the use of 4% PFA.

Several methods for mounting the cell sample between the slide and the cover slip were tested, notably Eukitt Mounting Medium (ProSciTech), Fluoromount-G (SouthernBiotech), and Prolong Gold Reagent (Invitrogen, Molecular Probes). The best results in terms of the exploitability of the autofluorescence of the cell samples were noted with Prolong Gold Reagent.

4) Demonstration of the Exploitability of the Autofluorescence of BAL Cells Taken from a Murine Model of Pneumonia.

With regard to the model of staphylococcal pneumonia, a strain of methicillin-sensitive *Staphylococcus aureus* (MSSA) (strain ATCC 29213) was grown for 16 hours at 37° C. in tryptic soy medium. Immediately before use, the cultures were washed twice (centrifuged for 10 minutes at 1000 g) and diluted in sterile isotonic saline serum to be calibrated by spectroscopy. The bacterial concentration was systematically monitored by quantitative culture.

With regard to the model of *Pseudomonas aeruginosa* pneumonia, a wild-type *Pseudomonas aeruginosa* strain was grown for 18 hours at 37° C. in tryptic soy liquid medium. Immediately before the intratracheal instillation, the cultures were washed twice (centrifuged for 10 minutes at 5000 g at 37° C.) and diluted in sterile isotonic serum to be calibrated by spectroscopy, followed by calibration by nephelometry to obtain a concentration of $1 \cdot 10^6$ CFU/ml. The control is prepared on Cetrimide agar (selective medium for *Pseudomonas aeruginosa*).

The mice were anaesthetized with isoflurane, and were placed in the decubitus dorsal position. An enteral feeding needle (24 gauge) was used for the catheterization of the trachea and the injection of 70 µl of bacterial solution (*Staphylococcus* or *Pseudomonas aeruginosa*). The mice were then suspended by the incisors for 30 seconds to improve the penetration of the inoculum. The intratracheal instillation rate reached 100%.

Twenty-four hours later, immediately after euthanasia, a bronchoalveolar lavage was carried out by catheterizing the trachea by percutaneous route (24 gauge catheter). Washes with 3×1 ml of physiological saline solution were then carried out. A cell count using a Malassez counting chamber was then carried out. The alveolar lavage fluid was then centrifuged (10 minutes at 5000 g at 37° C.) and the cell pellet was resuspended in physiological saline solution q.s. $1 \cdot 10^6$ cells/ml.

A 500 µl volume of cell sample ($5 \cdot 10^5$ cells) was delicately withdrawn and deposited in a well coupled to a microscopy slide in accordance with the Cytospin® device. A centrifugation-slide projection cycle was carried out at 600 rpm for 8 minutes with a low acceleration-deceleration. The cell spot projected on the slide was fixed with a drop of 4% paraformaldehyde (PFA) for 10 minutes followed by 3 delicate rinses with PBS buffer solution. After complete drying, a 20 µl drop of ProLong® Gold Antifade reagent mounting medium freshly unfrozen was deposited on the fixed cell spot. A glass cover slip was then delicately placed on the drop of mounting medium while taking care to avoid any formation of air bubbles.

The proportion of various PNN/macrophage cell types present in the alveolar lavage fluid was characterized (Giemsa staining):

| | Number of cells (/µl) | Macrophages (%) | Polymorphonuclear neutrophils (%) |
|---|---|---|---|
| Sham | 338 ± 230 | 67 ± 5* | 33 ± 5 |
| *Staphylococcus aureus* | 343 ± 161 | 7 ± 4 | 93 ± 4* |
| *Pseudomonas aeruginosa* | 255 ± 57 | 20 ± 9 | 80 ± 9* |

*$p < 0.05$ versus Sham

A highly significant increase in the number of PNN cells in relation to macrophages is observed in the mice having been inoculated with one or the other of the bacterial solutions (*Staphylococcus* or *Pseudomonas aeruginosa*). The percentages of polymorphonuclear neutrophils observed in the infected animals in relation to the control animals (sham) confirm the presence of a bacterial pneumonopathy.

The sample slides thus obtained were then observed using a confocal laser scanning microscope. For the acquisition of the fluorescence intensity signal, the continuous argon UV laser source was used ($\lambda=364$ nm, P=1.3 mW), as well as a photomultiplier (gain=1250 V) in the wavelength range of 400 nm to 550 nm, with a pinhole opened to the ⅓ of the maximum opening, and a X63 oil immersion objective. A mean of 4 images at a resolution of 1024 pixels/1024 pixels for a final size of 246 µm/246 µm was applied to display the image in $I_f$.

Twenty-nine mice were studied with 8 control mice, 9 mice with *Pseudomonas aeruginosa* pneumonia, and 12 mice with *Staphylococcus* pneumonia. The mean cellular autofluorescence intensity decreases for the slides from the mice with pneumonia in relation to the cells from the BAL from the control mice. The majority of cells (PNN) from the BAL of the mice with pneumonia fluoresce less than those from the BAL of the control mice (44.8 AU vs 107.5 AU). A factor of 2 exists between the mean autofluorescence intensity of the cells from the BAL of the mice with pneumonia and the mean autofluorescence intensity of the cells from the BAL of the control mice. These results make it possible to distinguish cells arising from the BAL of the control mice and the cells arising from the BAL of the mice suffering from pneumonia; this determination is based on a difference in mean autofluorescence intensity. The observation of an variation of the autofluorescence signal of the cells from the BAL of the infected mice opposite that of the monocytes in the model of stimulation ex vivo, confirms that the majority of the cells contained in the BAL of the infected mice consist of PNN. This result is thus in agreement with the decrease in the autofluorescence intensity of the PNN stimulated ex vivo in relation to the non-stimulated PNN controls in the preceding model of the cytology of cells stimulated ex vivo. The difference in the direction of the variation of the mean autofluorescence intensity between stimulated PNN and monocytes probably lies in their notable differences in terms of energy metabolism and of means of defense against the pathogen that leads to their stimulation.

BIBLIOGRAPHICAL REFERENCES

Babior B. M. et al., *Blood* 1984; 64: 959-966.
Brun-Buisson C et al. *Intensive Care Med* 2004; 30: 580-588.
E. Pilly, *Maladies infectieuses et tropicales*, 22$^{nd}$ Edition, 2010.
Keneth M. Murphy, Paul Travers, & Mark Walport, *Janeway's Immunobiology*. 7$^{th}$ Edition (Chapter 2, Innate Immunity).
Li B H et al., *World J. Gastroenterol.* 2006; 24: 1213-1217.
Martin G S et al., *N Engl J Med* 2003; 348: 1546-1554.
Mayevsky A et al., *Am J. Physiol. Cell Physiol.* 2007; 292: C615-640
Monici M., *Biotechnol Annu Rev.* 2005; 11: 227-56.
Palmer G M et al., *Photochem Photobiol* 2003; 78: 462-469.
Pauly J. L et al., *Microsc Res Tech* 2005; 67: 79-89.
Petty H. R. et al., PNAS 2001, vol. 98, no. 6, 3145-3149.

The invention claimed is:

1. An in vitro method for diagnosing the infectious state of an individual, comprising at least the following steps:
   i) measuring the mean cellular NAD(P)H autofluorescence intensity of a sample of leukocytes of a fluid arising from an organ of said individual with a fluorescence microscope that excites the cells with a wavelength ranging from 300 nm to 600 nm; and
   ii) comparing the intensity measured in step i) with a control value, so as to determine the infectious state of said individual.

2. The method according to claim 1, characterized in that the leukocytes of said sample are selected from monocytes and/or polymorphonuclear neutrophils.

3. The method according to claim 1, characterized in that, when the state of said individual is infectious, said individual is suffering from a bacterial, viral or fungal infection.

4. The method according to claim 1, characterized in that said fluid is a pulmonary fluid, ascites fluid, cerebrospinal fluid or fluid of any other potentially infected organ.

5. The method according to claim 1, characterized in that the autofluorescence intensity of the cells of said sample is measured on cells in suspension.

6. The method according to claim 1, characterized in that the autofluorescence intensity of the cells of said sample is measured on cells that are chemically fixed and placed on a slide compatible with the observation of fluorescence.

7. The method according to claim 1, wherein said sample of cells is prepared in a monolayer on a slide of transparent material prior to step i), according to a method comprising at least the following steps:
   a) depositing cells of said sample in at least one cytocentrifugation system;
   b) centrifuging so as to project the cells on said slide;
   c) chemically fixing the cells thus projected on the slide to form a cell spot, with at least one drop of about 4% paraformaldehyde (PFA);
   d) rinsing the previously fixed cell spot;
   e) allowing the previously rinsed cell spot to dry;
   f) adding to the previously dried cell spot at least one drop of a mounting medium compatible with the observation of fluorescence;
   g) affixing a transparent cover slip on the cell spot arising from step f).

8. The method of claim 7, wherein the at least one centrifugation system is centrifuged at about 600 rpm for about 5 minutes.

9. The method of claim 7, wherein chemically fixing the cells thus projected on the slide to form a cell spot are comprises chemically fixing with at least one drop of about 4% paraformaldehyde (PFA) for about 10 minutes.

10. The method of claim 7, wherein the previously fixed cell spot is rinsed with phosphate buffered saline (PBS) buffer.

11. The method of claim 7, wherein the transparent cover slip is a transparent glass cover slip.

12. The method according to claim 1, characterized in that, when the leukocytes of said sample are mostly polymorphonuclear neutrophils, the state of said individual is infectious if the autofluorescence intensity measured in step i) is significantly lower than the control value.

13. The method of claim 1 characterized in that, when the state of said individual is infectious, said individual is suffering from a bacterial infection.

14. The method of claim 1 characterized in that the autofluorescence intensity of the cells of said sample is measured on cells that are chemically fixed and placed on a transparent glass slide.

* * * * *